(12) United States Patent  
Cappa et al.

(10) Patent No.: US 7,092,761 B1  
(45) Date of Patent: Aug. 15, 2006

(54) TELEMETRY WAND WITH DISPLAY AND CONTROL FOR IMPLANTABLE MEDICAL DEVICES

(75) Inventors: Armando M. Cappa, Granada Hills, CA (US); Jeffrey D. Konopka, San Jose, CA (US); Rita M. Theis, Shakopee, MN (US)

(73) Assignee: Pacesetter, Inc., Sylmar, CA (US)

( * ) Notice: Subject to any disclaimer, the term of this patent is extended or adjusted under 35 U.S.C. 154(b) by 264 days.

(21) Appl. No.: 10/289,696

(22) Filed: Nov. 6, 2002

(51) Int. Cl.  
*A61N 1/32* (2006.01)
(52) U.S. Cl. .................................................... 607/60
(58) Field of Classification Search ............... 607/27, 607/32, 36, 59, 60; 128/903, 904  
See application file for complete search history.

(56) References Cited

U.S. PATENT DOCUMENTS 5,336,245 A * 8/1994 Adams Theodore et al. .. 607/32  
6,283,245 B1 * 9/2001 Thurman et al. ............. 607/60

* cited by examiner

*Primary Examiner*—George Manuel

(57) ABSTRACT

A programmer system for implantable devices including a programmer and a telemetry wand joined by a telemetry cable or via wireless. The telemetry wand includes at least partial display and control functionality for the system. The telemetry wand and telemetry cable are encapsulated to facilitate ready sterilization of the same and may be removably connected to the programmer. The system enables a clinician to remain within a sterile field, such as during an implantation procedure, and employ the programmer system while maintaining the sterile field without requiring that the entire programmer system be sterilized.

31 Claims, 5 Drawing Sheets

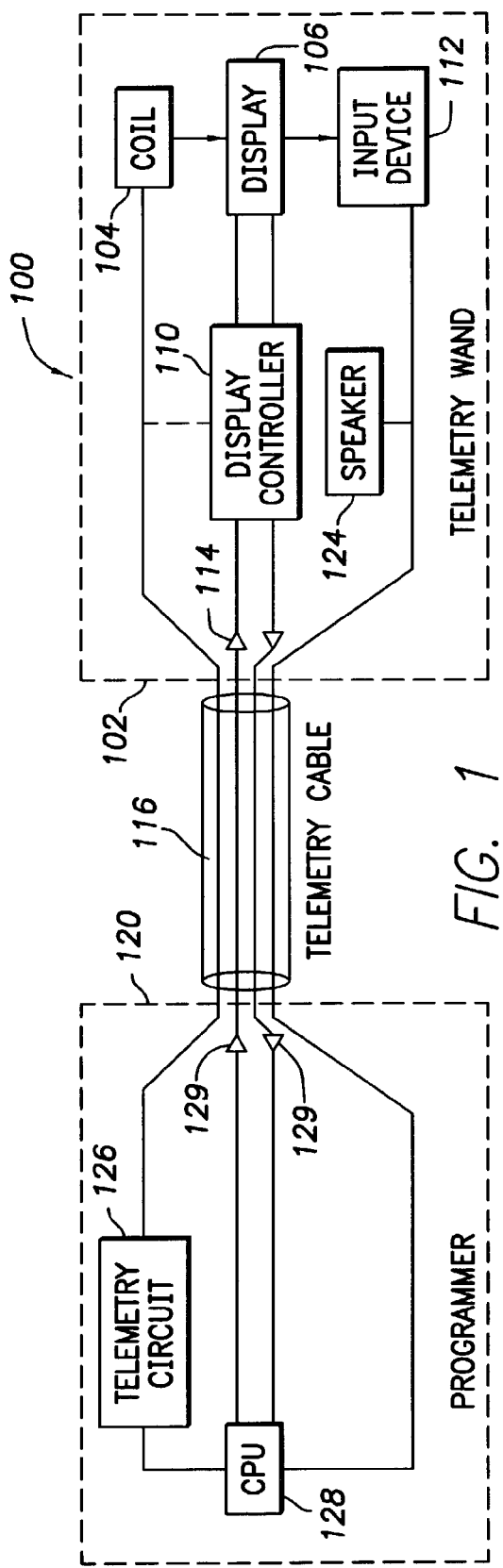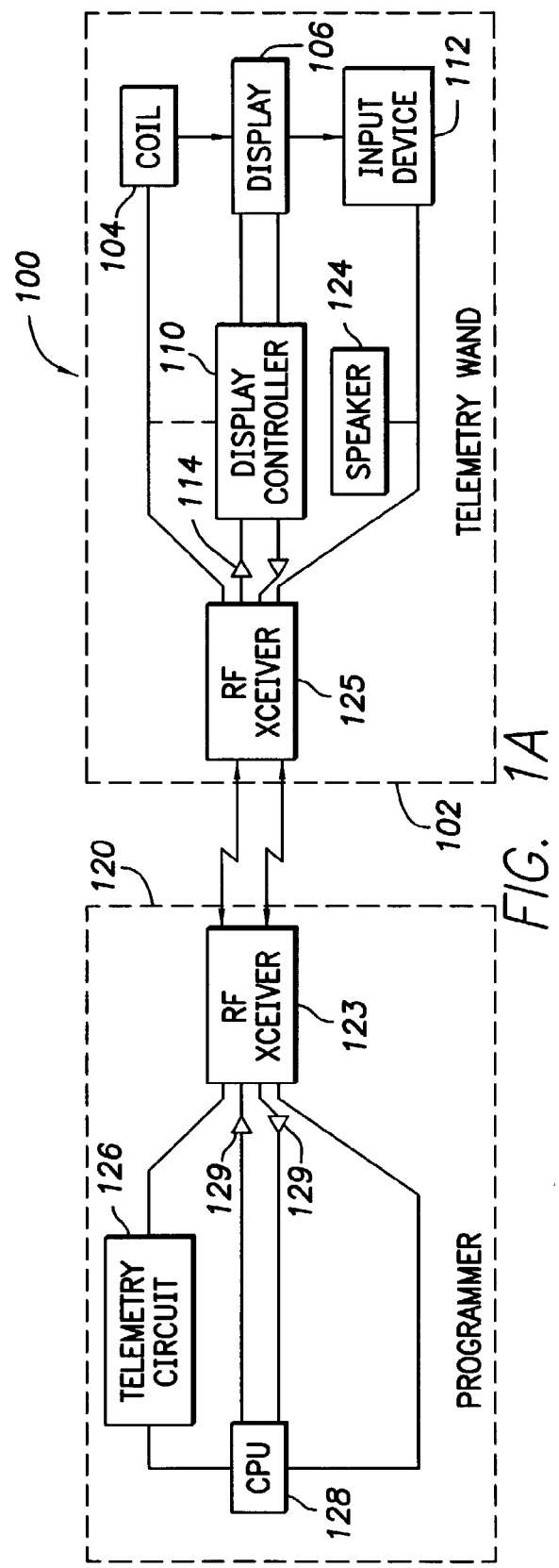

TELEMETRY WAND WITH DISPLAY AND CONTROL FOR IMPLANTABLE MEDICAL DEVICES

RELATED APPLICATIONS

This application is related to copending U.S. patent application Ser. No. 10/123,944, filed Apr. 16, 2002, titled Programmer and Surface ECG System with Wireless Communication; and Ser. No. 10/205,650, filed Jul. 24, 2002, titled "Programmer with Wireless Portable Display/Controller.

FIELD OF THE INVENTION

The invention relates to implantable medical devices and in particular to a telemetry wand for an implantable medical device programmer wherein the telemetry wand includes display and data input devices.

BACKGROUND OF THE INVENTION

The initial and ongoing clinical care provided to patients with implantable cardiac device systems often includes the use of programmers. A programmer is a device that enables a clinician to telemetrically communicate with and control an implantable cardiac device such as a pacemaker or defibrillator. Implantable devices often monitor and record a variety of internal physiological parameters of the patient and are often provided with a telemetry system to telemetrically transmit those measured and recorded parameters outside the patient's body to a programmer. A clinician can then review the data via the programmer and make any indicated changes in the patient's therapy.

Implantable devices are also often capable of receiving telemetric signals from a programmer to induce the device to set or change a variety of operational parameters of the device related to the therapy provided by the device as well as to select among the physiological parameters that the device monitors and records. These parameters are often desirably changed during the implantation period to adjust the therapy provided and/or the physiological parameters monitored in order to provide the attending clinician with different information or to adapt the therapy to a more efficacious regimen. It is highly desirable to set these parameters without the expense and health risks to the patient of additional invasive procedures and programmers enable the attending clinician to perform these tasks in a non-invasive, telegraphic manner after implantation with the insight of information provided from internal measurements provided by the device itself.

Accordingly, programmers typically include a display to visually present alphanumeric and graphical information relating to device performance and patient condition as well as user input devices to facilitate data entry and control inputs to be provided by a clinician to control device operation telemetrically. As implantable devices are typically battery powered, thus having also limited electrical power capacity, and, as telemetric communication is a relatively major source of battery depletion, programmers often include a movable wand with an antenna that is placed on the patient overlying the implanted device to receive and send signals to/from the implantable device. The wand is also placed over the implanted device to be proximate the device to thereby limit RF interference with other nearby devices. The telemetry wand with antenna is typically specially adapted for efficient establishment of a telemetric link between the programmer and the implantable device so as to minimize the power that the implantable device must provide to achieve the telemetric link thereby reducing the drain on the battery of the implantable device.

Programmers are particularly useful during the implantation process as the telemetric feedback from the device to the programmer can confirm integrity of the connections of leads to the implantable device as the leads are attached or, conversely, indicate faulty connections thereof. The implantable device can also telemetrically indicate its operational status to the programmer and it will be understood by one of skill in the art that correct device operation is preferably confirmed before closure of surgical incisions.

It will also be appreciated that the actual implantation procedure calls for a sterile environment to reduce risk of infections and complications for the implantee. Thus, it is desirable that not only the implantable device and any leads, but other operating room equipment in contact with the patient, such as a programmer be maintained sterile at least during invasive procedures, such as implantation.

However, it is problematic to sterilize electronic devices, such as programmers, because of their composition and construction. Thus, it is often the practice to interconnect a telemetry wand to the programmer via a relatively long (typically greater than 3 m) cable. The wand and cable are generally encapsulated in such a manner that the wand and cable can be readily sterilized such as by autoclaving or Ethylene Oxide (ETO) gas, without damaging the programmer or requiring that the programmer itself be sterilized. The sterilized wand and cable can then be placed in proximity to the implantee while maintaining an adequate distance from the unsterilized programmer.

However, the distancing between the wand and the programmer also presents some difficulties in use for the clinician. In particular, as previously mentioned, the programmer and wand are a useful tool to the implanting clinician to confirm attachment of leads to the implantable device and to confirm proper device operation and activation prior to closure of surgical incisions. However, the programmer with the display is typically located outside the sterile field and thus outside of the field of view of the implanting clinician. This imposes the burden of providing additional attending staff to convey to the implanting clinician the information provided by the programmer. It can be understood that this presents an added cost and inconvenience and a possible source of error in verbally conveying the information provided in a graphical manner at the programmer.

From the foregoing it can be appreciated that there is an ongoing need for a programmer that provides the ability for a clinician to directly access at least part of the display and control input capability of a programmer from within a sterile field.

SUMMARY

The aforementioned needs are satisfied by the invention, which in one aspect, is a programmer system capable of telemetrically communicating with implantable medical devices so as to transceive data therewith, the system including a telemetry circuit capable of transceiving data with the implantable devices, a telemetry wand including a display and data input device in communication with the telemetry circuit, a programmer in communication with the telemetry circuit, and a communication cable interconnecting the telemetry wand and the programmer such that the telemetry wand can be distanced from the programmer and such that at least some of the data transceived with the implantable device may be viewed via the display of the wand and such that the implantable device may be at least partially controlled via the input device of the wand. In, another aspect, communication between the telemetry wand and programmer is performed by wireless communication, e.g., radio-frequency (RF) communication.

In certain aspects, the telemetry wand includes an antenna adapted for tranceiving data with the implantable devices. In other aspects, the communication cable and the programmer further comprise mating connectors to allow the telemetry wand to be removably connected to the programmer, and/or the communication cable and the telemetry wand are encapsulated so as to facilitate sterilization of the communication cable and the telemetry wand. In additional aspects, the telemetry wand can be distanced from the programmer such that the telemetry wand is in a sterile field adjacent the implantable device and the programmer is located outside of the sterile field.

In particular aspects, the data that may be viewed via the wand includes currently set base rate of the implantable device and the at least partial control that can be asserted via the wand includes setting the base rate of the implantable device.

Yet another aspect further includes a surface physiological monitor providing signals indicative of patient condition, which may comprise a surface electrocardiogram (ECG) monitor and wherein a surface ECG waveform provided by the surface ECG monitor may be viewed via the telemetry wand. A surface electrocardiogram monitor typically comprises a plurality of electrodes that are attached to the patients body so as to provide electrical signals indicative of the heart activity to a central monitor. These signals can provide different representations of the heart activity as seen along different vectors based on the relative positions of the electrodes.

The invention also includes the aspect of an implantable medical device system comprising an implantable medical device including a telemetry system capable of sending and receiving electronic signals, a programmer system capable of transceiving electronic signals with the implantable medical device, the programmer system comprising a telemetry wand including an antenna adapted to transceive signals with the implantable device and a display and data input device, a programmer, and a communication cable interconnecting the telemetry wand and the programmer such that information transceived between the implantable device and the programmer system may be at least partially viewed via the display of the telemetry wand and such that at least partial control of the programmer system and implantable device can be effected via the input device of the telemetry wand.

In certain of these aspects, the telemetry wand may further include an antenna adapted for tranceiving data with the implantable devices and in addition or alternatively, the communication cable and the programmer may further comprise mating connectors to allow the telemetry wand to be removably connected to the programmer.

A particular aspect is wherein the communication cable and the telemetry wand are encapsulated so as to facilitate sterilization of the communication cable and the telemetry wand, and this in aspect the telemetry wand may be distanced from the programmer such that the telemetry wand is in a sterile field adjacent the implantable device and the programmer is located outside of the sterile field.

Yet another aspect is wherein the data that may be viewed via the wand includes the currently set base rate of the implantable device and/or wherein the at least partial control that can be asserted via the wand includes setting the base rate of the implantable device.

An additional aspect may further comprise a surface physiological monitor providing signals indicative of patient condition that may comprise a surface ECG monitor and wherein a surface ECG waveform provided by the surface ECG monitor may be viewed via the telemetry wand and display.

The invention is also a programmer system capable of telemetrically communicating with implantable medical devices so as to transceive data therewith, the system including telemetry means capable of transceiving data with the implantable devices, a telemetry wand including display means and data input means in communication with the telemetry means, a programmer in communication with the telemetry means, and a communication cable interconnecting the telemetry wand and the programmer such that the telemetry wand can be distanced from the programmer and such that at least some of the data transceived with the implantable device may be viewed via the display means of the wand and such that the implantable device may be at least partially controlled via the data input means of the wand.

In particular aspects thereof, the telemetry means comprises a radio-frequency transceiver and/or the display means comprises a liquid crystal or similar display. These and other objects and advantages will be more apparent from the following description taken in conjunction with the accompanying drawings.

BRIEF DESCRIPTION OF THE DRAWINGS

FIG. 1 is a high-level block diagram of one embodiment of a programmer system with telemetry wand with display and control;

FIG. 1A is a high-level block diagram of another embodiment of a programmer system and telemetry wand;

DETAILED DESCRIPTION OF THE PREFERRED EMBODIMENT

Reference will now be made to the drawings wherein like numerals refer to like parts throughout. FIG. 1 is a functional block diagram of one embodiment of a programmer system with telemetry wand with display and control for implantable medical devices 100, referred to hereafter as system 100 for brevity. The system 100 facilitates communication with an implantable medical device (not shown) in a manner that facilitates maintenance of a sterile field around an implantee, reduces the need for attending personnel in the clinical setting, and provides increased convenience of use with the system 100.

Figure 4:
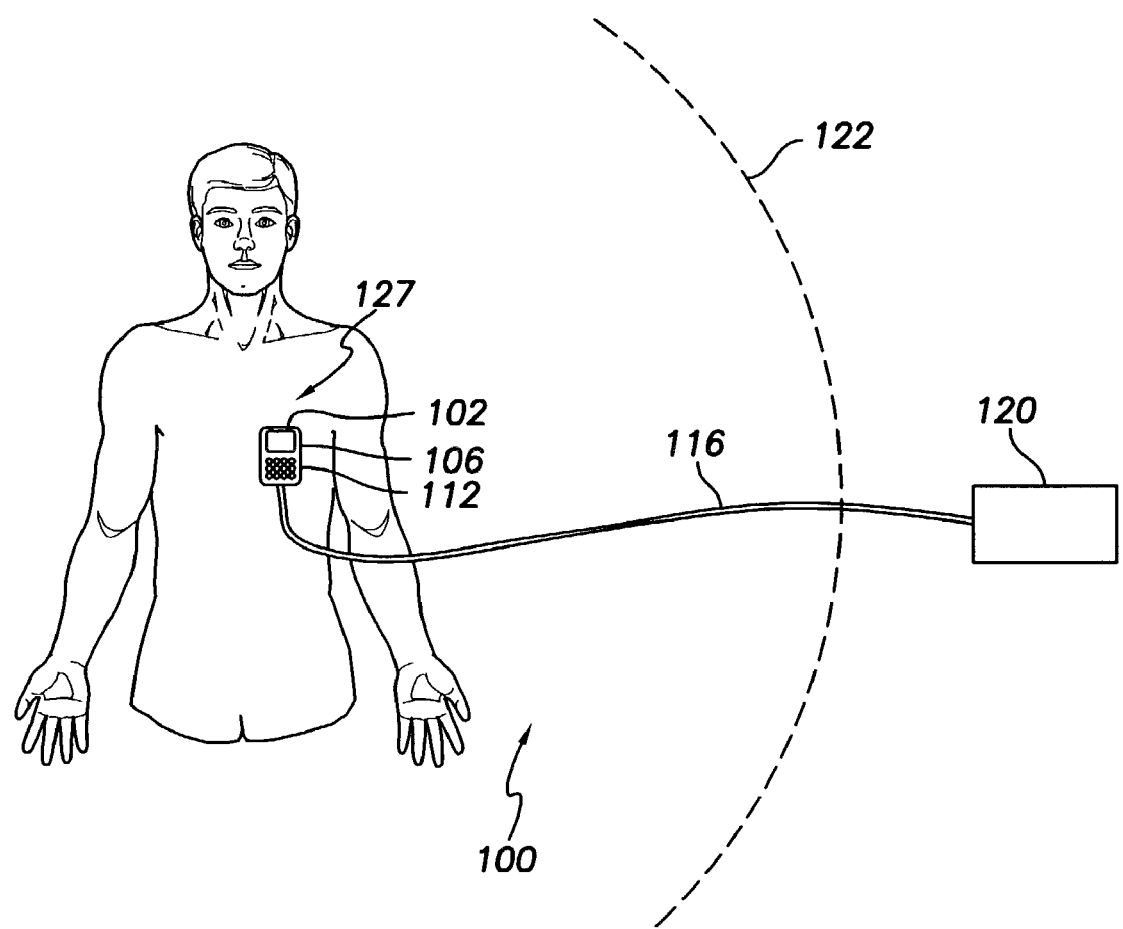
FIG. 4 is a front view of one manner of employing the system of FIG. 1.

The system 100 comprises a telemetry wand 102 and a programmer 120 joined by a telemetry cable 116 or wireless telemetry link (FIG. 1A). The telemetry wand 102 is adapted to be placed adjacent an implantable device, such as may be surgically implanted in a patient thorax as shown in FIG. 4, and to transceive electronic signals therewith and to exchange the signals with the programmer 120 via the telemetry cable 116 or wireless link. In certain embodiments, the telemetry wand 102 also receives electrical operating power from the programmer 120 via the telemetry cable 116. The telemetry wand 102 may be employed to communicate with an implantable device either during an implantation procedure or, following implantation, to reprogram, reconfigure, and/or extract information from the implantable device.

The telemetry wand 102 includes a coil 104. The coil 104 is configured as a radio-frequency (RF) antenna to facilitate communication between the implantable device and the system 100. The construction of the coil 104 is well understood by one of ordinary skill in the art. The composition and form of the coil 104 can vary in specific applications and may preferably be configured to enable telemetric communication between the system 100 and the implantable device at increased data rate and reduced power expended by the implantable device. The coil 104 is in communication with the programmer 120 via the telemetry cable 116 so as to be able to exchange signals therewith. In an alternate embodiment shown in FIG. 1A, coil 104 is in communication with programmer 120 via RF transceivers 123 and 125.

The telemetry wand 102 also comprises a display 106. The display 106 presents alphanumeric and graphical information relating to patient condition, implantable device performance and status, etc. to a user of the system 100. The display 106 can comprise a liquid-crystal display (LCD), plasma display, array of light-emitting diodes (LEDs), or other display means capable of visually presenting information to a user. In certain embodiments, the display 106 can provide full display capability for the system 100 and, in other embodiments, the display 106 is capable of displaying a selected subset of the display capability of the system 100. Specific examples of the information that can be provided by the display 106 will be described in greater detail below with reference to the functions provided by the programmer 120.

The telemetry wand 102 also comprises a display controller 110 and amplifiers 114 in communication with the display 106. In certain embodiments, the display controller 110 is adapted to receive data from the programmer 120 via the telemetry cable 116 and amplifiers 114 and format the data for presentation on the display 106. The amplifiers 114 provide electronic gain to signals passed on the telemetry cable 116 between the telemetry wand 102 and the programmer 120 in a well understood manner. In certain embodiments, the display controller 110 is in communication with the coil 104 (as indicated with the dashed line therebetween in FIG. 1) and includes the capability of processing signals received from the coil 106 so as to allow the display controller 110 to provide signals to the display 106 separately from the programmer 120.

The telemetry wand 102 also comprises at least one input device 112. The input device 112 can comprise a keyswitch matrix, keyboard, microphone and corresponding speech recognition software, and/or can be embodied as a touchscreen aspect of the display 106. The input device 112 enables a user to input information and to select among various operational controls of the telemetry wand 102 and system 100. In the embodiments wherein the input device 112 comprises touchscreen aspects of the display 106, the display controller 116 and amplifiers 114 are adapted to format and amplify the signals provided by the input device 112 for communication to the programmer 120.

In certain embodiments, the input device 112 comprises programmable and/or special function keys providing predefined functions of the system 100. Specific examples of functions and inputs available to a user via the input device 112 of the telemetry wand 102 will be described in greater detail below with reference to functions provided by the programmer 120.

Figure 2:
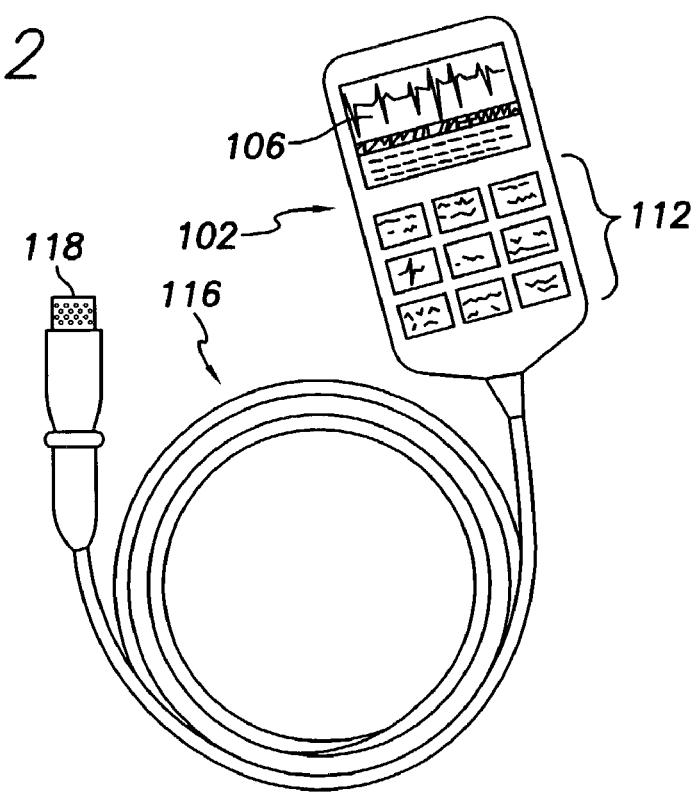
FIG. 2 is a top view of one embodiment of the telemetry wand with display and control of FIG. 1.

FIG. 2 is a top view of one embodiment of the telemetry wand 102 in greater detail and shows the telemetry wand 102 with the display 106. The telemetry wand 102 of this embodiment also includes a connector 118 adapted to physically and electrically mate with the programmer 120 in a detachable manner so as to allow communication between the telemetry wand 102 and the programmer 120 via the telemetry cable 116 and the connector 118. In certain embodiments, the telemetry cable 116 and connector 118 can comprise an industry standard format, such as a Universal Serial Bus (USB) format, and in other embodiments, the telemetry cable 116 and connector 118 are specifically custom adapted for specific applications.

The telemetry wand 102, including the telemetry cable 116 and connector 118 in this embodiment, are encapsulated so as to facilitate sterilization of the telemetry wand 102 and telemetry cable 116, such as via autoclaving, treatment with ethylene oxide (ETO) gas, or other known methods of sterilizing medical equipment. In certain embodiments, the telemetry cable 116 is preferably at least approximately 3 m in length. This aspect of the system 100 provides the advantage that the sterilized telemetry wand 102 and telemetry cable 116 can be placed within a sterile field 122 in clinical setting as shown in FIG. 4 while the telemetry cable 116 and connector 118 extend outside of the sterile field 122 for connection to the programmer 120. The programmer 120 thus can remain outside the sterile field 122 and thus does not need to be sterilized to maintain the integrity of the sterile field 122.

A further advantage of this aspect of the system 100 is that a clinician, such as a physician performing an implantation procedure of an implantable device, can remain in the sterile field 122 adjacent the patient and access the capability of the system 100 via the telemetry wand 102 while a portion thereof, such as the programmer 120, does not need to be sterile being located outside of the sterile field 122. Specifically, the system allows a clinician to provide input commands to the system 100 via the input device 112 of the telemetry wand 102 to induce the system to telemetrically communicate with the implantable device via the coil 104. The system 100 also allows a clinician to telemetrically receive and view data from the implantable device via the coil 104 and presents the information on the display 106 of the telemetry wand 102 while remaining in the sterile field 122. This aspect of the system 100 reduces the need for additional clinical personnel who may be outside the sterile field 122 to relay information to a clinician within the sterile field 122.

In certain embodiments, the telemetry wand 102 also comprises a speaker 124. The speaker 124 provides audible alerts and informational tones to a user in a manner well understood in the art. In certain embodiments, the telemetry wand 102 can establish confirmation of a telemetry link 127 with the implantable device via a confirmed feedback signal or "handshaking" in a variety of manners known in the art. Upon establishment of the telemetry link 127, the system 100 can provide an audible indication, such as a specific tone, series of tones, or spoken words, via the speaker 124 and/or a visual indication via the display 106 to indicate proper positioning of the telemetry wand 102 with respect to the implantable device and the patient. This aspect of the system 100 also offers the advantage that a clinician can receive data from the system 100 while located in the sterile field 122 and while a portion of the system 100, such as the programmer 120, remains outside the sterile field 122 without the assistance or requirement for additional personnel.

Figure 3:
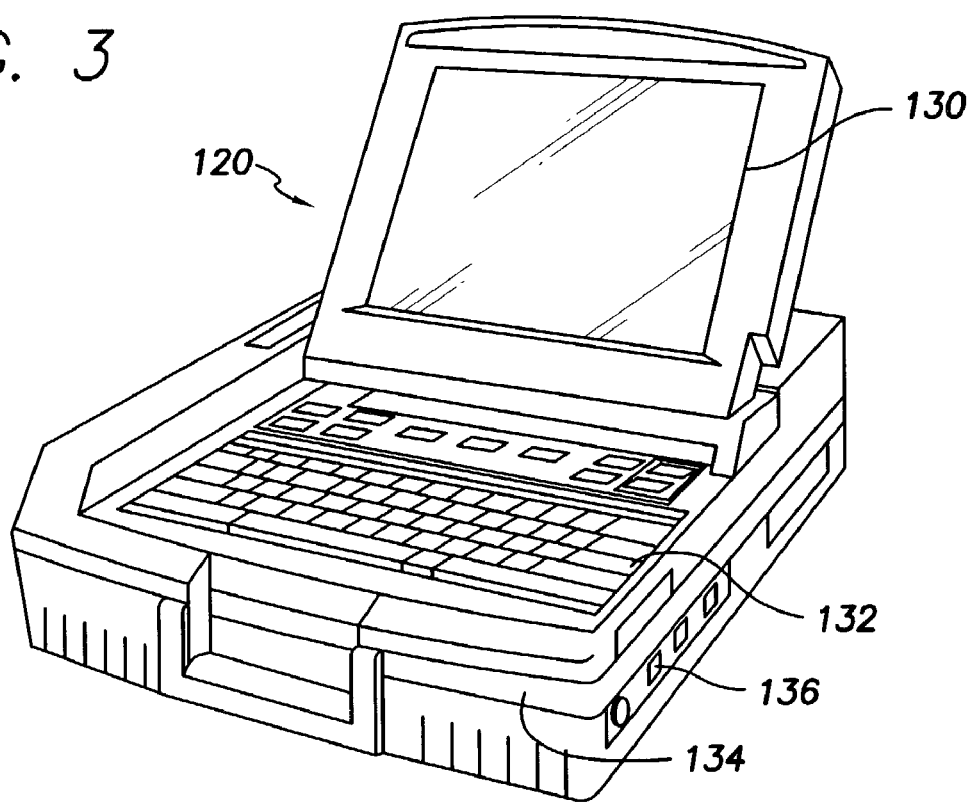
FIG. 3 is a perspective view of one embodiment of a programmer of the programmer system of FIG. 1.

FIG. 3 is a perspective view of one embodiment of the programmer 120 of the system 100. The programmer 120 is a stationary portion of the programmer system 100 and includes typically bulkier items and/or items that are more power consumptive than those of the aspects of the programmer system 100 embodied in the telemetry wand 102. The programmer 120 also comprises portions of the programmer system 100 that do not need to be in close proximity to patients in order to permit proper operation of the system 100 as provided with the telemetry wand 102. In certain embodiments, the programmer 120 is provided with line electrical service for electrical power and thus has practically an unlimited amount of electrical power available. In other embodiments, the programmer 120 is provided with a portable electrical power source, such as batteries, (not shown) to enable the system 100 to be more readily portable. As previously mentioned, in certain embodiments, the telemetry wand 102 receives operational electrical power from the programmer 120 via the telemetry cable 116 and thus, in these certain embodiments, the telemetry wand 102 receives electrical power from a line source or a portable source in accordance with the programmer 120.

The programmer 120 comprises a telemetry circuit 126 (FIG. 1). The telemetry circuit 126 is adapted to allow the programmer 120 to establish at least one wireless telemetry link 127 (FIG. 4) with implantable devices via the coil 104 of the telemetry wand 102 and the telemetry cable 116. It will be appreciated that as the system 100 may receive line power that offers practically unlimited power, the coil 104 of the telemetry wand 102 may have a higher energy delivery rate than the corresponding devices of the implantable device. As telemetry rate is generally dependent on power available, it is anticipated that the wireless communication between the telemetry wand 102 and implantable devices may occur at a differential speed, i.e., transmission from the implantable device may occur at a slower speed than transmission to the implantable device.

In certain embodiments, the programmer 120 also comprises a central processing unit (CPU) 128 (FIG. 1). The CPU 128 is adapted to process digital information and execute programmable functions and is commercially available. The CPU 128 is in communication with the telemetry wand 102 via amplifiers 129 and the telemetry cable 116. The CPU 128 also controls the operation of the programmer 120 as will be described in greater detail below with reference to FIG. 5.

In the embodiment shown in FIG. 3, the programmer 120 also comprises a display 130. The display 130 presents alphanumeric and graphical information relating to patient condition, implantable device performance and status, etc. to a user of the system 100. The display 130 can comprise a liquid-crystal display (LCD), plasma display, array of light-emitting diodes (LEDs), or other display means capable of visually presenting information to a user. In certain embodiments, the display 130 is larger than the display 106 and thus can more readily provide full display capability for the system 100. In these embodiments, the display 106 is capable of displaying a selected subset of the display capability of the system 100.

In the embodiment shown in FIG. 3, the programmer 120 also comprises an input device 132, a removable storage device 134, and a connector 136. The input device 132 enables a user to input information and to select among various operational controls of the system 100. The input device 132 of the embodiment shown in FIG. 3 comprises a keyboard and a plurality of special function keys, however, in other embodiments, the input device can further comprise a keyswitch matrix, microphone and corresponding speech recognition software, and/or can be embodied as a touchscreen aspect of the display 106.

The removable storage device 134 provides the capability of storing data on a removable media in a non-volatile manner. The removable storage device 134 in the embodiment shown in FIG. 3 comprises a removable disk, however, in other embodiments the removable storage device 134 can alternatively or in addition comprise a non-volatile solid state storage system, such as a flash memory system or an optical storage system, such as a writeable optical disc. The connector 136 is adapted to physically and electrically mate with the connector 118 so as to allow the telemetry cable 116 and thus the telemetry wand 102 to be removably connected to the programmer 120.

Figure 5:
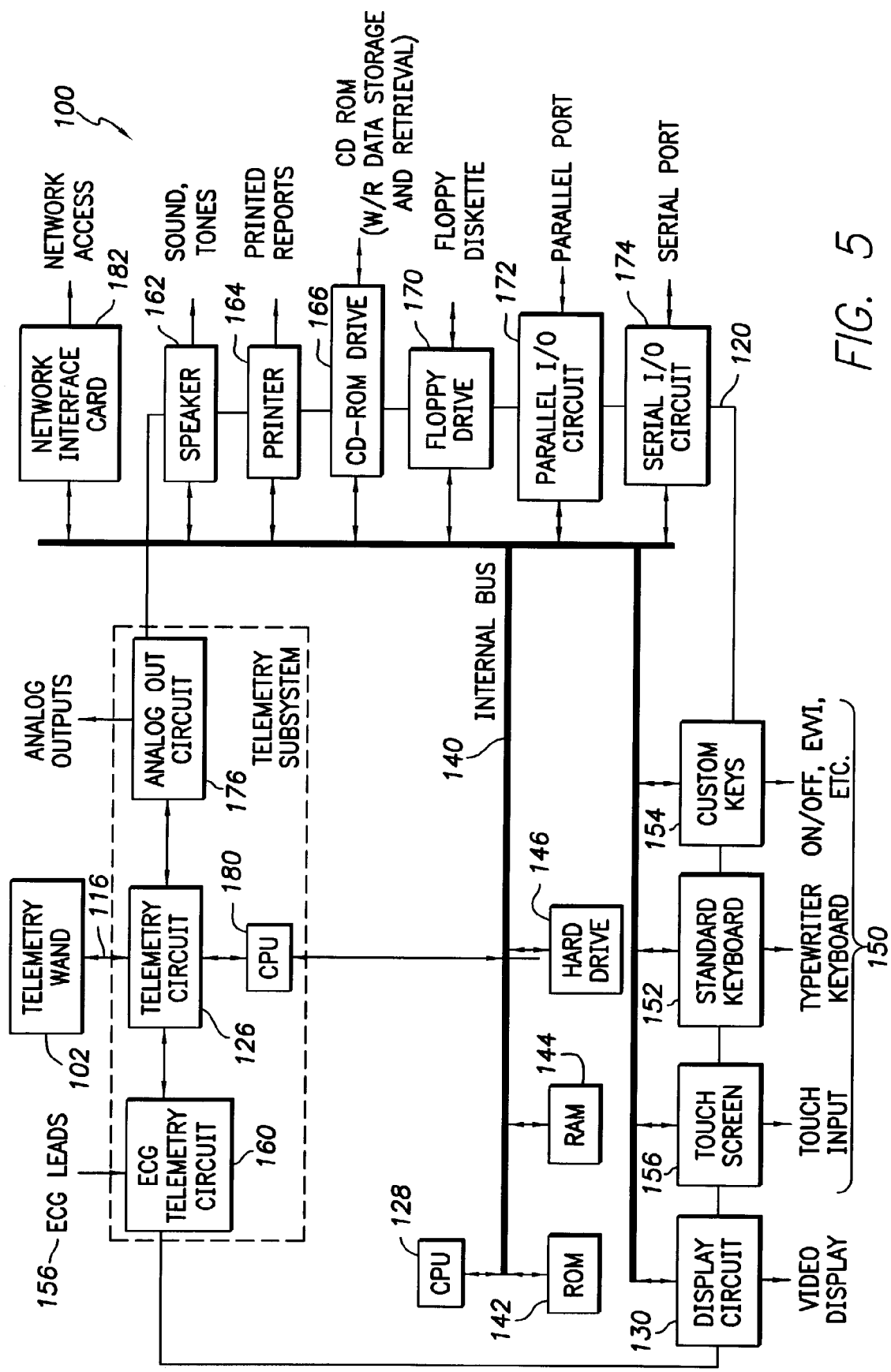
FIG. 5 is a functional block diagram of the programmer of the programmer system of FIG. 1.

FIG. 5 is a functional block diagram of one embodiment of the programmer 120 illustrating greater details thereof. The CPU 128 is in communication with an internal bus 140. The internal bus 140 provides a common communication link and power supply between the various electrical devices of the programmer 120, including the CPU 128. The programmer 120 also comprises ROM 142, RAM 144, and a hard drive 146 in communication with the internal bus 140. The ROM 142, RAM 144, and hard drive 146 provide temporary memory and non-volatile storage of data in a well known manner. In particular, the ROM 142, RAM 144, and hard drive 146 can store programmed control programs and commands for upload to an implantable device as well as control programs for display of data received from an implantable device as is well understood in the art. It will be appreciated that, in certain embodiments, alternative data storage/memory devices, such as flash memory, can be included or replace at least one of the ROM 142, RAM 144, and hard drive 146 without detracting from the spirit of the invention.

In certain embodiments, the programmer 120 also comprises input devices 150 comprising, in this embodiment, a keyboard 152, a plurality of custom keys 154, and a touchscreen 158 aspect of the display 130. The keyboard 152 facilitates entry of alphanumeric data into the programmer system 100. The custom keys 154 are programmable in order to provide one touch functionality of predefined functions and/or operations of the system 100. The custom keys 154 may be embodied as dedicated touch keys and/or as predefined areas of the touchscreen 158. The custom keys 154 can provide overlapping, i.e., identical functions to those provided by the input device 112 of the telemetry wand 102, however, the custom keys 154 can also provide additional functions than the input device 112.

In various embodiments of the system 100, functions provided by at least one of the input devices 150 of the programmer 120 and the input device 112 of the telemetry wand 102 include selection of an electrocardiogram (ECG) and/or an intracardiac electrogram (IEGM) for display on the display 130. An ECG signal is displayed in accordance with surface signals received from the patient via a plurality of ECG leads 156 in a manner well understood by one of ordinary skill in the art. In the embodiment illustrated in FIG. 5, the ECG leads 156 provide signals to an ECG circuit 160 of the system 100. In various embodiments, the system 100 then displays the ECG waveform in a variety of known formats, such as a Lead I, Lead II, or Lead III configuration on at least one of the displays 106, 130. The input devices 112, 150 also provide the capability for a user to select among the various lead configurations available. An IEGM provides similar information to a user as an ECG, except that ECG provides information relating to cardiac activity as measured on the surface of the patient's skin while an IEGM provides internal measurements, such as provided by an implantable device via the telemetry link 127.

Another function that is provided, in certain embodiments, by at least one of the input devices 112, 150 includes access to an automatic physician follow-up diagnostic to verify/monitor device operation, patient condition, records of past anomalous cardiac events, records of therapy provided, implantable device battery charge state, etc. In certain embodiments, the system 100 can also provide emergency ventricular inhibited pacing (VVI) and/or fibrillation shock activation via at least one of the input devices 112, 150. The system 100 can also provide a feedback indication of placement of the telemetry wand 102 with respect to an implantable device via a signal strength indication on at least one of the displays 106, 130 and/or via the amplitude or tone of an audible indicator. The input devices 112, 150 can also provide up-down scrolling through available functions or operations as well as selection of available functions.

Figure 6:
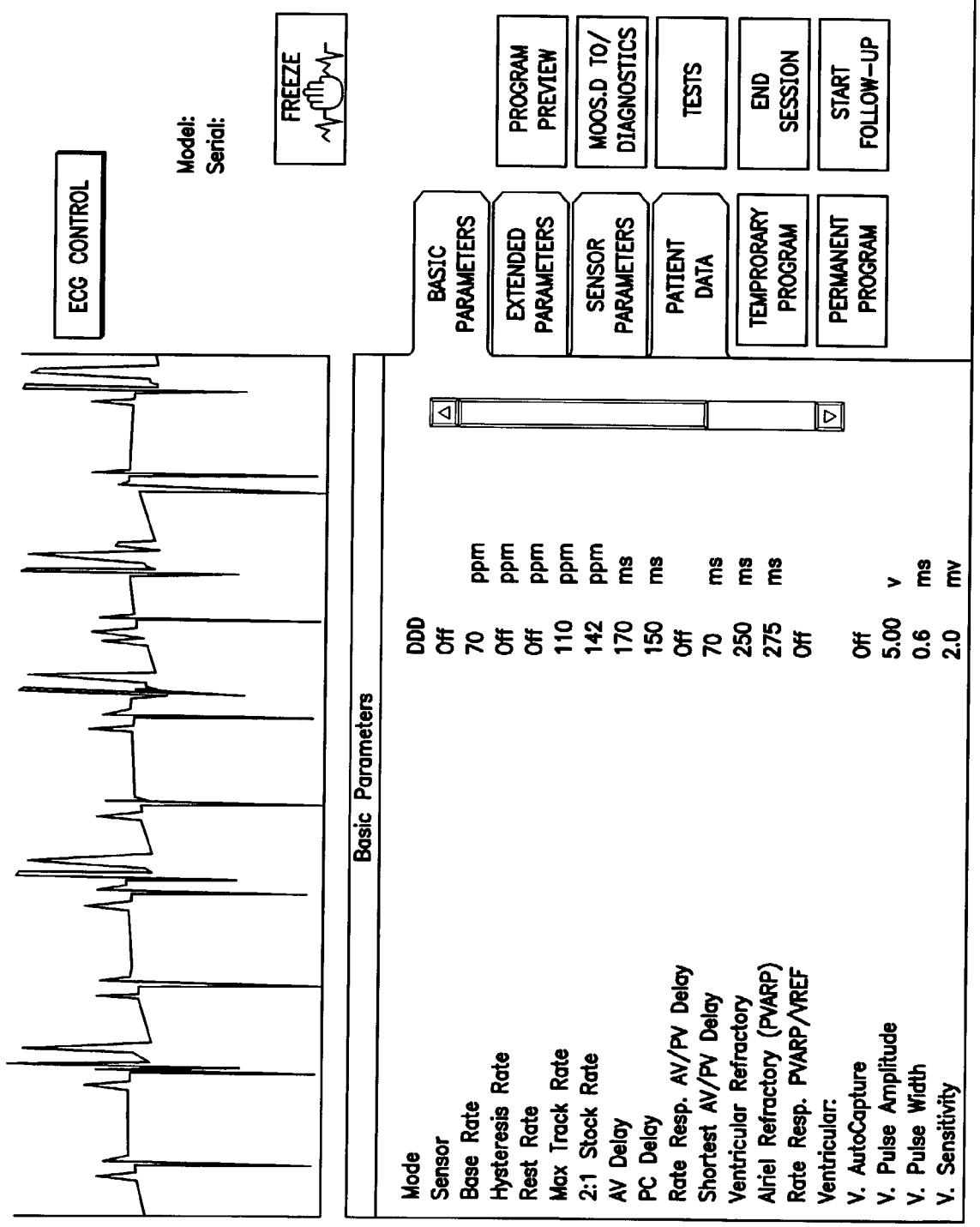
FIG. 6 is a screen-shot of one embodiment of a display of the system of FIG. 1 indicating information and controls that can be provided via the telemetry wand.

FIG. 6 illustrates one embodiment of functions and information that can be displayed on the displays 106, 130. However, it is to be understood that a variety of additional functions and data can be provided and made available via the input devices 112, 150 and the displays 106, 130 in various embodiments of the system 100 without detracting from the scope of the invention. It should also be understood that the functions and data made available via the displays 106, 130 and the input devices 112, 150 can be programmable and that the functions and data used in a specific application may be a subset of a broader set available via the system 100.

The display 106, 130 in the embodiment shown in FIG. 6 presents a surface ECG waveform and a plurality of user selectable status fields including base rate, ventricular refractory, etc. The display 106, 130 also presents functions that may be selected or deselected via the system 100, such as ventricular autocapture, which, in this embodiment, is deselected. The system 100 also provides the capability to telemetrically set operating parameters of the implantable device, such as the base rate, which in this example is currently set at 70 paced beats per minute (ppm). The display 106, 130 provides the ability to scroll through a window to view additional information and/or available functions. The display 106, 130 of this embodiment also provides the custom keys 154 that provide selection among, for example, display of sensor parameters, patient data, etc. It should be appreciated that, in certain embodiments, the display 106, 130 can comprise aspects of the input devices 112, 150 such as the touch screen 156. Certain aspects of the input devices 112, 150 can also comprise aspects of the display 106, 130, such as the custom keys 154 that include a data input function and also a data display function.

In certain embodiments, the programmer 120 also comprises a speaker 162 and a printer 164 in communication with the internal bus 140. The speaker 162 is adapted to provide audible alerts and signals to a user and the printer 164 is adapted to provide a printed read-out of information as generated or monitored by the system 100.

The programmer 120 can also comprise a CD drive 166 and a floppy drive 170 which together comprise the removable storage 134. The CD drive 166 and the floppy drive 170 provide removable data storage and read capability for the programmer system 100 in a well understood manner.

In this embodiment, the programmer 120 also provides interfaces including a parallel input-output (IO) circuit 172, a serial IO circuit 174, an analog output circuit 176, and network interface card 182. These interfaces 172, 174, 176, 182 provide a variety of communication capability with other devices and/or networks in a manner well understood in the art.

In this embodiment, the programmer 120 further includes a telemetry CPU 180 that facilitates the establishment and maintenance of the telemetry link 127. It is to be understood that the components of the system 100 described above are exemplary and that additions or deletions of certain elements may be made without detracting from the spirit of the invention.

It will be understood from the foregoing description that the telemetry wand 102 acts both as a display and control device for a clinician user as well as a telemetry relay/repeater enabling the telemetry link 127 between the implantable device, the telemetry wand 102, and the programmer 120. The system 100 facilitates ready sterilization of at least a portion thereof, such as the telemetry wand 102 and telemetry cable 116. The system 100 enables a single clinician to employ the system 100 within a sterile field 122 while maintaining the integrity of the sterile field 122 and the ability to access at least a portion of the display and control functionality of the system 100 without requiring that the entire system 100 be sterilized.

Although the preferred embodiments of the present invention have shown, described and pointed out the fundamental novel features of the invention as applied to those embodiments, it will be understood that various omissions, substitutions and changes in the form of the detail of the device illustrated may be made by those skilled in the art without departing from the spirit of the present invention. Consequently, the scope of the invention should not be limited to the foregoing description but is to be defined by the appended claims.

What is claimed is:

1. A programmer system capable of telemetrically communicating with implantable medical devices so as to transceive data therewith, the system comprising:
   a telemetry circuit capable of transceiving data with the implantable devices;
   a programmer in communication with the telemetry circuit;
   a telemetry wand comprising a display and data input device in communication with the telemetry circuit, wherein the data input device of the telemetry wand is adapted to generate control signals that provide user control over one or more pacing parameters of the implantable medical devices independently from operation of the programmer; and
   a communication cable interconnecting the telemetry wand and the programmer and operative to transmit data between the telemetry wand and the programmer.

2. The system of claim 1, wherein the telemetry wand comprises an antenna adapted for transceiving data with the implantable devices.

3. The system of claim 1, wherein the communication cable and the programmer further comprise mating connectors to allow the telemetry wand to be removably connected to the programmer.

4. The system of claim 1, wherein the communication cable and the telemetry wand are encapsulated so as to facilitate sterilization of the communication cable and the telemetry wand.

5. The system of claim 1, wherein the telemetry wand can be distanced from the programmer such that the telemetry wand is in a sterile field adjacent the implantable device and the programmer is located outside of the sterile field.

6. The system of claim 1, wherein the data that may be viewed via the wand comprises a currently set base rate of the implantable device.

7. The system of claim 1, wherein the at least partial control that can be asserted via the wand comprises setting the base rate of the implantable device.

8. The system of claim 1, further comprising a surface physiological monitor providing signals indicative of patient condition.

9. The system of claim 8, wherein the surface physiological monitor comprises a surface ECG monitor and wherein a surface ECG waveform provided by the surface ECG monitor may be viewed via the telemetry wand.

10. An implantable medical device system comprising:
an implantable medical device comprising a telemetry system capable of sending and receiving electronic signals;
a programmer system capable of transceiving electronic signals with the implantable medical device, the programmer system comprising:
a telemetry wand comprising an antenna adapted to transceive signals with the implantable device and a display and data input device;
a programmer adapted to provide independent user control of the implantable device; and
a communication cable interconnecting the telemetry wand and the programmer such that information transceived between the implantable device and the programmer system may be at least partially viewed via the display of the telemetry wand by a user adjacent the implantable device and wherein the data input device of the telemetry wand is adapted to generate control signals that provide independent from the programmer, user control of the programmer or the implantable device.

11. The system of claim 10, wherein the telemetry wand comprises an antenna adapted for transceiving data with the implantable devices.

12. The system of claim 10, wherein the communication cable and the programmer further comprise mating connectors to allow the telemetry wand to be removably connected to the programmer.

13. The system of claim 10, wherein the communication cable and the telemetry wand are encapsulated so as to facilitate sterilization of the communication cable and the telemetry wand.

14. The system of claim 10, wherein the telemetry wand can be distanced from the programmer such that the telemetry wand is in a sterile field adjacent the implantable device and the programmer is located outside of the sterile field.

15. The system of claim 10, wherein the data that may be viewed via the wand comprises a currently set base rate of the implantable device.

16. The system of claim 10, wherein the at least partial control that can be asserted via the wand comprises setting the base rate of the implantable device.

17. The system of claim 10, further comprising a surface physiological monitor providing signals indicative of patient condition.

18. The system of claim 17, wherein the surface physiological monitor comprises a surface ECG monitor and wherein a surface ECG waveform provided by the surface ECG monitor may be viewed via the telemetry wand.

19. A programmer system capable of telemetrically communicating with implantable medical devices so as to transceive data therewith, the system comprising:
telemetry means for transceiving data with the implantable devices;
a programmer;
a telemetry wand comprising display means and data input means wherein the data input means of the telemetry wand is adapted to provide user control of one or more pacing parameters of the implantable devices independently from the programmer, wherein the telemetry wand is in communication with the telemetry means; and
means for transmitting data between the telemetry wand and the programmer.

20. The system of claim 19, wherein the telemetry means comprises a radio-frequency transceiver.

21. The system of claim 19, wherein the display means comprises a liquid crystal display.

22. The system of claim 19, wherein the data input means comprises a plurality of key switches.

23. The system of claim 19, further comprising a physiological monitoring means providing signals to the programmer system indicative of patient condition such that the signals provided by the physiological monitoring means may be displayed via the display means.

24. The system of claim 23, wherein the physiological monitoring means provides surface ECG signals.

25. A method of communicating with an implantable device so as to provide control inputs and receive data therewith, the method comprising:
positioning a telemetry wand adjacent the implantable device;
telemetrically communicating signals with the implantable device via the telemetry wand;
communicating the signals to a programmer;
processing the signals;
displaying at least a portion of the processed signals via the telemetry wand;
generating control signals via an input device of the telemetry wand independently from the programmer for altering one or more pacing parameters of the implantable medical device; and
providing the control signals to the implantable device to modify the one or more pacing parameters of the implantable device via the telemetry wand.

26. The method of claim 25, wherein displaying the processed signals comprises displaying data relating to present device operation.

27. The method of claim 26, wherein data relating to device operation comprises a currently set base rate of the device.

28. The method of claim 25, wherein displaying the processed signals comprises displaying signals corresponding to patient condition.

29. The method of claim 28, wherein signals corresponding to patient condition comprise an IEGM waveform.

30. The method of claim 25, wherein providing control signals comprises providing control signals altering device operation.

31. The method of claim 30, wherein altering device operation comprises altering a currently set base rate of the device.

* * * * *